(12) United States Patent
Yue

(10) Patent No.: US 6,306,593 B1
(45) Date of Patent: *Oct. 23, 2001

(54) SELECTIVE AFLP PRIMERS FOR REDUCTION OF COMPLEXITY OF MAKER GENOTYPING AND DNA MARKERS FOR LOBLOLLY PINE IDENTIFIED USING THE AFLP PRIMERS

(75) Inventor: Yong G. Yue, Trenton, NJ (US)

(73) Assignee: Union Camp Corporation, Princeton, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/157,351

(22) Filed: Sep. 17, 1998

(51) Int. Cl.[7] ............... C12Q 1/68; C12Q 1/44; C12P 19/34; C07H 21/04
(52) U.S. Cl. .................. 435/6; 435/19; 435/91.2; 536/23.1; 536/24.3; 536/24.33
(58) Field of Search ................... 435/6, 19, 91.2; 536/23.1, 24.3, 24.33

(56) References Cited

U.S. PATENT DOCUMENTS

| | | | | |
|---|---|---|---|---|
| 4,965,188 | * | 10/1990 | Mullis | 435/6 |
| 6,045,994 | * | 4/2000 | Zabeau et al. | 435/6 |
| 6,218,119 | * | 4/2001 | Kuiper et al. | 435/6 |

OTHER PUBLICATIONS

Vos, P. et al. Nucleic Acids Research 23(21):4407–4414, 1995.*
Grattapaglia, D. et al. Genetics 144:1205–1214, Nov. 1996.*
Groover, A. et al. Genetics 138:1293–1300, Dec. 1994.*

* cited by examiner

*Primary Examiner*—Carla J. Myers
*Assistant Examiner*—Diana Johannsen
(74) *Attorney, Agent, or Firm*—Licata & Tyrrell P.C.

(57) ABSTRACT

Selective AFLP primers which decrease the complexity of marker genotyping having a variable region of four or more selective nucleotides and a constant region of nucleotides which match base pairs of a restriction fragment of a selected frequent cutter enzyme are provided. AFLP primers and specific DNA markers for volume growth of loblolly pine are also provided. In addition, methods for identifying and selecting loblolly pine trees for greater volume growth are described.

5 Claims, 4 Drawing Sheets

FIGURE 4 ucc101 (SEQ ID NO:1; 139 bp):

```
  1    GACTGCGTAC ATGCAGGAAG CAATGTGAAT TGTAATAGAA
 41    GCAATTGCCC AAGAACAATC AATAAAATAC CACAATAAAG
 81    NAAGCAGTGT TTCCCATTTG GGTTTCCTAG GTAAACAAGT
121    GTGTTACTCA GGACTCATC
``` ucc102 (SEQ ID NO:2; 134 bp):

```
  1    GACTGCGTAC ATGCAGATAA TCAGTGAGAT ATTTAGTTTT
 41    TGATCCTGTT CATGGAAATT GTACACCTAC AATATCCGAA
 81    GCACATAAAG GTGGCTTATG ACTTCTCTCC ATTTATACTT
121    ACTCAGGACT CATC
``` ucc103 (SEQ ID NO:3; 90 bp):

```
  1    GACTGCGTAC ATGCAGGAAG TAATACAGTC AAATTGGGAA
 41    CCGCGGAGGG AAAATTGTTT TTTCAATTGT CCACTTACTC
 81    AGGACTCATC
```

SELECTIVE AFLP PRIMERS FOR REDUCTION OF COMPLEXITY OF MAKER GENOTYPING AND DNA MARKERS FOR LOBLOLLY PINE IDENTIFIED USING THE AFLP PRIMERS

BACKGROUND OF THE INVENTION

DNA fingerprinting or DNA typing involves the display of a set of DNA fragments from a selected DNA sample. In almost all living organisms with the exception of viruses, restriction digests of the total genomic DNA of the organism yield so many bands that it is not possible to score individual bands. Accordingly, fingerprinting methods are based on the principle that only a small fraction of the DNA fragments are visualized so as to yield a simple banding pattern which makes up the DNA fingerprint. A variety of techniques for DNA fingerprinting are currently available.

Until recently, the most widely used method for DNA fingerprinting was Southern hybridization. This procedure requires digesting the DNA of the organism with restriction endonuclease, fractionating the restriction fragments by gel electrophoresis, transferring and binding the fractionated DNA fragments onto membranes and hybridizing the membrane with a specific DNA fragment or probe. The probe forms a double-stranded DNA molecule with the DNA fragment or fragments on the membrane having complementary nucleotide sequences. The probe is typically tagged with a visible marker for easy detection of the DNA fragment. DNA polymorphisms, and more specifically restriction fragment length polymorphisms, are identified by differences in size of the corresponding restriction fragments to which the probe attaches. However, Southern hybridization is both laborious and time consuming.

Accordingly, a number of DNA fingerprinting techniques have been developed which use polymerase chain reaction (PCR) for detection of fragments. The selection of the fingerprinting technique to use is dependent upon the application, i.e., DNA marker typing, DNA typing, and the organism and size of the genome of the organism. Preferably, the fingerprinting technique requires no prior sequence analysis, primer synthesis or characterization of DNA probes. A number of fingerprinting techniques which meet these criteria have been developed. These include random amplified polymorphic DNA (RAPD; Williams et al. Nucleic Acid research 1990 18:6531–6535), DNA amplification fingerprinting (DAF; Caetano-Anolles et al. Bio/Technology 1991 9:553–557) and arbitrarily primed PCR (AP-PCR; Welsh, J. And McClelland, M. Nucleic Acid Research 1990 18:7213–7218). However, these PCR based fingerprinting methods are very sensitive to reaction conditions, DNA quality and PCR temperature profiles, thus limiting their use.

Amplified fragment length polymorphisms (AFLP) is a newer method for DNA fingerprinting involving application of PCR to amplify one or more restriction fragments from complex mixtures of DNA fragments obtained by digesting a genomic DNA molecule with restriction endonuclease. The general method for AFLP is disclosed by Zabeau and Vos in PCT Application WO 93/06239. In this method, primers used for amplification are not directed against a known DNA sequence but rather are designed such that they recognize the ends of the restriction fragments. The PCR primers taught by Zabeau and Vos comprise a constant nucleotide sequence part and a variable nucleotide sequence part. The constant sequence part of the nucleotide sequence is designed so that the primer matches with the base pairs of one of the DNA strands at the end of the restriction fragment. The variable sequence part designates a sequence consisting of selected nucleotides forming a sequence which then remains constant during amplification of a subset of restriction fragments and directs that preselection of tagged restriction fragments to be amplified in the PCR step. Selection is determined by the number of nucleotides residing in the variable length part of the primer. These are referred to as selective bases or selective nucleotides. Selectivity of the primer is suggested to theoretically increase with the number of selective nucleotides in the variable sequence part.

A number of examples of DNA fingerprinting via AFLP are disclosed in PCT Application WO 93/06239 with primers having a constant nucleotide part which matches the base pairs of various restriction fragments of cutting enzymes including PstI, MseI, EcoRI, Taq, AseI and Sse8387-I and variable regions with 1 to 3 selective nucleotides. Also disclosed is a primer set with a constant nucleotide part which matches the restriction fragment of the rare cutting enzyme, PstI, and variable regions with 5 selective nucleotides. Rare cutting enzymes are characterized by having a restriction site of 6 or more nucleotides.

More recent studies by Vos et al. (Nucleic Acid Research 1995 23(21):4407–4414), however, indicate that primers for frequent cutter enzymes, e.g., MseI, lose selectivity if more than 3 selective nucleotides are incorporated into the variable region. Vos et al. teach a loss of selectivity with primers having four selective bases illustrated by numerous bands not detected in the corresponding fingerprints with primers having three selective bases. This is suggested to be indicative of the tolerance of mismatches in the amplification fragments using AFLP primers with four-base extensions.

In the present invention AFLP primers for frequent enzyme cutters which contain four or more selective nucleotides are provided which are able to maintain their selectivity while reducing complexity and increasing specificity in marker genotyping. In these primers, one or more nucleotides of the constant region of the AFLP primer are truncated as additional selective nucleotides are added to the variable region of the AFLP primer so that the length of the primer remains relatively the same. These AFLP markers are particularly useful in marker genotyping of large genomes. DNA markers for volume growth in loblolly pine have now been identified using AFLP primers of the present invention.

SUMMARY OF THE INVENTION

An object of the present invention is to provide selective AFLP primers for frequent cutter enzymes which comprise a variable region of four or more selective nucleotides and a constant region of nucleotides which match the base pairs of a selected restriction fragment of a frequent cutter enzyme. In a preferred embodiment, nucleotides of the constant region are truncated to compensate for the number of selective nucleotides in the variable region so that the length of the primer and its melting temperature remain relatively constant.

Another object of the present invention is to provide a method for fingerprinting DNA by AFLP using these selective AFLP primers.

Another object of the present invention is to provide a set of primers for identifying a DNA marker for volume growth in loblolly pine.

Another object of the present invention is to provide a DNA marker associated with volume growth in loblolly pine.

Another object of the present invention is to provide a method for identifying genes that control volume growth in loblolly pine.

Another object of the present invention is to provide a method for identifying volume growth potential in loblolly pine.

BRIEF DESCRIPTION OF THE DRAWINGS

FIG. 4 provides the nucleic acid sequences (5' to 3') of aca.gct.009-linked AFLP markers in loblolly pine, which are designated ucc101 (SEQ ID NO: 1), ucc102 (SEQ ID NO: 2) and ucc103 (SEQ ID NO: 3). AFLP primers are indicated by underlining. PstI primers are located at the 5' end of the nucleic acid sequences while MseI primers are located at the 3' end.

DETAILED DESCRIPTION OF THE INVENTION

Figure 1:
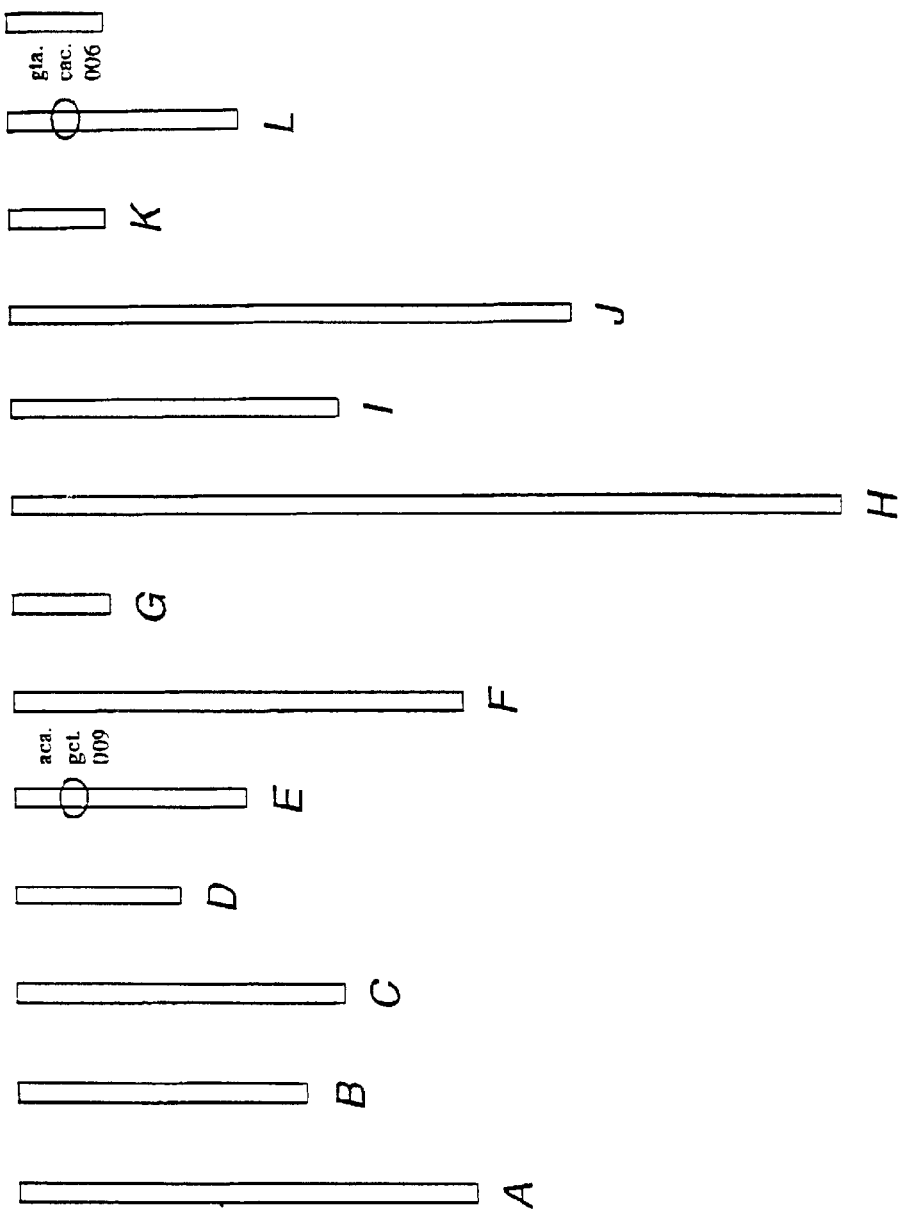
FIG. 1 is a genetic map showing the chromosomal location of the aca.gct.009 and gta.cac.006 DNA markers in 7-56 trees. The linkage groups in the parental lines are designated A-L.

Amplified fragment length polymorphism (AFLP) provides a powerful method of DNA fingerprinting and provides the most cost-effective means for producing DNA markers for genetic mapping in a wide range of species. Further, AFLP is in general a more effective method as compared to RFLP and RAPD because this technology can reveal more then 100 markers simultaneously. AFLP-based genetic markers have also been found to be more reproducible than RAPD. Specific AFLP marker bands that are linked to genes or quantitative traits can be rapidly identified by genetic mapping.

In some applications, such as breeding, selection and DNA fingerprinting organisms with large genome size, it is desirable to have less bands but more specific AFLP patterns. One drawback of AFLP technology is its dependence on the size of the genome, or the quantity of DNA sequences. The majority of agricultural crops have a genome size range from $0.4 \times 10^9$ base pairs (rice) to $2.3 \times 10^9$ base pairs (maize). However, some crops, such as pine trees have a genome size approximately 5 times that of maize and 27 times that of rice. The large number of DNA sequences from such a large genome causes difficulties in resolving AFLP bands.

In AFLP analysis, two restriction enzymes, typically EcoRI and MseI, are first used to cut DNA at specific sites to generate small fragments. Based on these restriction sites, a pair of synthetic oligonucleotide primers are used to amplify a subset of DNA fragments by PCR. After PCR reaction, the fragments are displayed as bands by electrophoresis in a polyacrylamide gel. The number of bands in a gel corresponds to the number of bands amplified by PCR. This is determined by the selective nucleotides in the primer. The conventional AFLP protocol was developed primarily with tomato DNA having a genome size of approximately 900 million base pairs and uses three selective nucleotides (MseI+3). The +3 primer works well with many plant and animal species whose genome size ranges from 500 to 3000 million base pairs.

However, in plants such as pine, the MseI +3 primers produce too many bands, resulting in reduced resolution in separating DNA fragments in the gels. Theoretically, the number of AFLP bands can be reduced by adding more selective nucleotides (e.g. MseI+4). However, it has been previously demonstrated that MseI+4 primers produced more bands than MseI+3 primers (Vos et al. *Nucleic Acid Research* 1995 23(21):4407–4414).

It has now been found, however, that AFLP primers for frequent cutter enzymes such as MseI which comprise 4 or more selective nucleotides in the variable region of the AFLP primer are highly selective and capable of decreasing the number of AFLP bands amplified by PCR to a desirable level regardless of genome size when nucleotides in the constant regions of the primer are truncated to compensate for increased length of the primer resulting from the extra selective nucleotides (see Table 1).

TABLE 1

The Effect of Additional Selective Nucleotides on the Length of Regular and Truncated AFLP primers

| MseI adaptor sequence: | | |
|---|---|---|
| | 5'gacgatgagtcctgag | taannnnn (SEQ ID NO: 4) |
| | Tactcaggactcat | tnnnnn (SEQ ID NO: 5) |
| ALFP MseI primers: | | |
| (+1) | gatgagtcctgagtaa C | (17 nt; SEQ ID NO: 6) |
| (+2) | gatgagtcctgagtaa CT | (18 nt; SEQ ID NO: 7) |
| (+3) | gatgagtcctgagtaa CTA | (19 nt; SEQ ID NO: 8) |
| (+4) | gatgagtcctgagtaa CTAC | (20 nt; SEQ ID NO: 9) |
| 5' truncated MseI primers: | | |
| (trun+4) | gagtcctgagtaa CTAC | (17 nt; SEQ ID NO: 10) |
| (trun+5) | gagtcctgagtaa CTACT | (18 nt; SEQ ID NO: 11) |
| Selective nucleotides of the primers are shown in this table in upper case letters. | | |

Additional selective nucleotides to be added to the AFLP primers of the present invention can be determined routinely by those of skill in the art by various means. In one embodiment, multiple primers with various random combinations of 4 or more nucleotides in the variable region and identical constant regions truncated to compensate for additional selective nucleotides are prepared. Amplification is then performed with the multiple primers and the resulting band patterns are compared to band patterns produced by commercially available AFLP primers with only 1 to 3 selective nucleotides. Primers which contain 4 or more "selective nucleotides" will decrease the number of amplified bands in the pattern as compared to commercially available AFLP primers with 1 to 3 selective nucleotides. However, the bands that are amplified by primers containing 4 or more selective nucleotides will be a subset of the bands amplified by the commercially available primers with 1 to 3 selective nucleotides. The amplified subset of bands is more easily interpreted because "noise" or genetically irrelevant bands are eliminated. In that the bands amplified are separated on the basis of base size, the more selective nucleotides can simplify banding patterns, thus reducing the likelihood of co-migrating bands.

In another embodiment of the invention, commercially available AFLP primers containing 1 to 3 selective nucleotides are used to isolate a selected DNA fragment. This selected DNA fragment is then cloned and sequenced to ascertain the identity of additional selective nucleotides which can be incorporated into the AFLP primers in accordance with teachings provided herein to increase the selectivity while reducing the complexity of the subset of DNA fragments generated by AFLP.

For the purposes of this invention, by "frequent cutter enzyme" it is meant a restriction enzyme with a restriction site of four or less nucleotides. Examples include, but are not limited to, AciI, AluI, BlaI, BstUI, CviJI, DpnI, DpnII, MaeII, MaeIII, MboI, MnlI, MseI, MspI, NlaIII, RsaI, Sau3AI, TaiI, TaqI, TscI and Tsp509I. For AFLP, MseI is commonly used. This is contrasted with "rare cutter enzymes", such as PstI, which have restriction sites of at least five or more nucleotides. Experiments with soybean (1,115 million base pairs), barley (4,873) and loblolly pine (11,580 million base pairs) confirmed the ability of these new +4 and +5 primers to increase selectivity while reducing the complexity of the subset of DNA fragments generated by AFLP of these plant species of varying genome size. These primers are particularly useful in AFLP analysis of large genome plant species including, but certainly not limited to, vanilla (7,672 million base pairs) and loblolly pine (11,580 million base pairs).

Loblolly pine is an important commercial forest tree in the United States and is grown for both wood and paper product purposes. Because of their physical size and the acreage needed to grow trees for 10 to 12 years to reach sexual maturity, large populations of full-sibling crosses to carry out genetic mappings for trees are generally not available. As a result, many genetic studies into specific traits for loblolly pine are conducted among study populations of half-siblings, i.e., trees having one parent in common, which necessarily complicates the genetic analysis. One of the specific factors those skilled in the art would like to study for evaluating growth in trees such as loblolly pine is volume growth; volume growth (cubic feet) is the product of tree height (feet) and tree diameter squared (square feet).

A set of quantitative trait loci (QTLs) with major effects on height annual increments was disclosed (Kaya et al. (1996. SRIEG Workshop, Houston, Tex., poster #12). However, the purported effects of these QTLs was inconsistent from year to year. Further, and more importantly, none of the QTLs in this set showed a discernable effect on cumulative volume growth. The effect of RAPD markers on annual measurements of a half-sib loblolly pine family has also been examined (O'Malley, D. M. et al. 1997. Plant & Animal Genome V Conference, San Diego, Calif., Workshop Presentation #W37). Results from these studies showed that some markers had effects in certain years, but not in others.

The selective primers of the present invention have now been used to identify and characterize new volume growth DNA markers in loblolly pine via AFLP. DNA markers identified using the primers of the present invention can be used as a guide to locate the gene or genes that regulate volume growth in loblolly pine, as well as to locate other DNA markers for volume growth. With the approximate location of growth-related genes now known in the loblolly pine genome, it is expected that additional DNA markers can be identified from these chromosomal regions based on the teachings of the present invention. Accordingly, the present invention also provides compositions and methods for identifying volume growth potential in loblolly pine.

The DNA markers of the present invention were identified from a family comprising tree clone 7-56. The 7-56 clone is one of the most widely planted loblolly pine families in the Southeastern U.S. and one of the most well-known loblolly pine clones (Neale, D. B. and R. R. Sederoff. 1996. In: A. H. Paterson (ed) *Genome Mapping in Plants* R. G. Landes Company, pp. 309–319). Progeny of 7-56 have been shown to be among the best height performers among the first generation selections and, more generally, one of the best growers from age one. Because it is so widely planted, the ability to develop DNA markers based on this clone is enhanced. The present invention is applicable to any breeding program wherein the trees carry the 7-56 parentage.

For the initial experiments, tree tissue samples were collected from a field site known as the Satilla site using an alcohol-based tissue preservation system that allows for shipment of samples for DNA analysis without special equipment for transport or preservation of the tissue samples. This preservation method requires at least a 1:10 ratio of tissue to alcohol for reliable tissue fixation. Tree tissue samples may be taken from any part of the tree including, but not limited to, needles, seeds or bark.

The trees sampled were 7-2×7-56 full-sib trees that were measured for their height and diameter at age ten. Using a total of 11 PstI/MseI primer combinations, genetic marker data were collected for 139 amplified fragment length polymorphisms (AFLP) bands in this 7-2×7-56 full-sib mapping population. Using a single-factor analysis of variance (ANOVA), three AFLP markers were shown to have a significant effect on the volume growth in these trees. These three markers were designated aca.gct.009, gta.cac.006, and ac.cacg.006. The designation for each primer is indicative of the primer and the band in the gel from which the marker was derived. For example, aca.gct.009 means that the marker was derived from PstI-aca and MseI-gct primers, and that it was the ninth (009) band from the top of the gel.

A conservative declaration of marker effect was made by applying a probability level of 0.01 (p-value); the probability of mistakenly picking up a false positive is less than 1%. In addition to volume growth, the three markers were assessed for their effect using the two measurements from which volume growth is derived, i.e., height and diameter. These results are shown in Table 2.

TABLE 2

The Effect of Marker Phenotype at Three Marker Loci on the Volume Growth of the 7-2 × 7-56 Full-Sib Trees (Satilla Data)

| Marker | AFLP Source[1] | 7-2 Type No.[2] | Aver- age[3] | 7-56 Type No. | Average | ANOVA Test F | p-value[4] |
|---|---|---|---|---|---|---|---|
| | | Volume Growth (cu. ft) | | | | | |
| aca.gct.009 | 7-56 | 98 | 13.5 | 80 | 16.8 | 13.11 | .0003* |
| gta.cac.006 | 7-56 | 102 | 13.8 | 82 | 16.4 | 7.70 | .0061* |
| ac.cacg.006 | 7-2 | 90 | 13.8 | 91 | 16.2 | 6.96 | .0090* |
| | | Height (ft) | | | | | |
| aca.gct.009 | 7-56 | 98 | 47.9 | 80 | 50.3 | 8.02 | .0052* |
| gta.cac.006 | 7-56 | 102 | 47.7 | 82 | 50.6 | 14.2 | .0002* |
| ac.cacg.006 | 7-2 | 90 | 48.0 | 91 | 50.0 | 6.36 | .0125 |
| | | Diameter (ft) | | | | | |
| aca.gct.009 | 7-56 | 98 | 0.51 | 80 | 0.56 | 8.69 | .0036* |

TABLE 2-continued

The Effect of Marker Phenotype at Three Marker
Loci on the Volume Growth of the
7-2 × 7-56 Full-Sib Trees (Satilla Data)

| | | 7-2 Type | | 7-56 Type | | ANOVA Test | |
|---|---|---|---|---|---|---|---|
| Marker | AFLP Source[1] | No.[2] | Aver-age[3] | No. | Average | F | p-value[4] |
| gta.cac.006 | 7-56 | 102 | 0.52 | 82 | 0.56 | 6.57 | .0111 |
| ac.cacg.006 | 7-2 | 90 | 0.52 | 91 | 0.55 | 4.25 | .0406 |

[1]The parental source of the AFLP marker band.
[2]The number of full-sib trees that have the corresponding AFLP marker type.
[3]The value for volume growth, height, or diameter averaged from all full-sib trees of that marker type.
[4]A probability value lower than 0.01 indicates a statistically significant marker effect. All significant p-values are marked with an asterisk (*).

As seen in Table 2, aca.gct.009 was the only marker with significant effects on both component trait(s) (height and diameter) for volume growth. The gta.cac.006 marker had an effect only on height, while ac.cacg.006 exhibited no effect on either trait. Using a two-gene model, the cumulative effect of both aca.gct.009 and gta.cac.006 on height, diameter, and volume growth was determined. Results showed that trees with both marker bands from 7-56 on average performed 12% better in terms of height, 18% better in terms of diameter, and 52% better in terms of volume growth. If these better performing full-sib trees were selected based on these two QTL markers, the selected trees would be expected to have an average improvement of 23% in volume growth over unselected 7-2×7-56 full-sib family trees.

Figure 2:
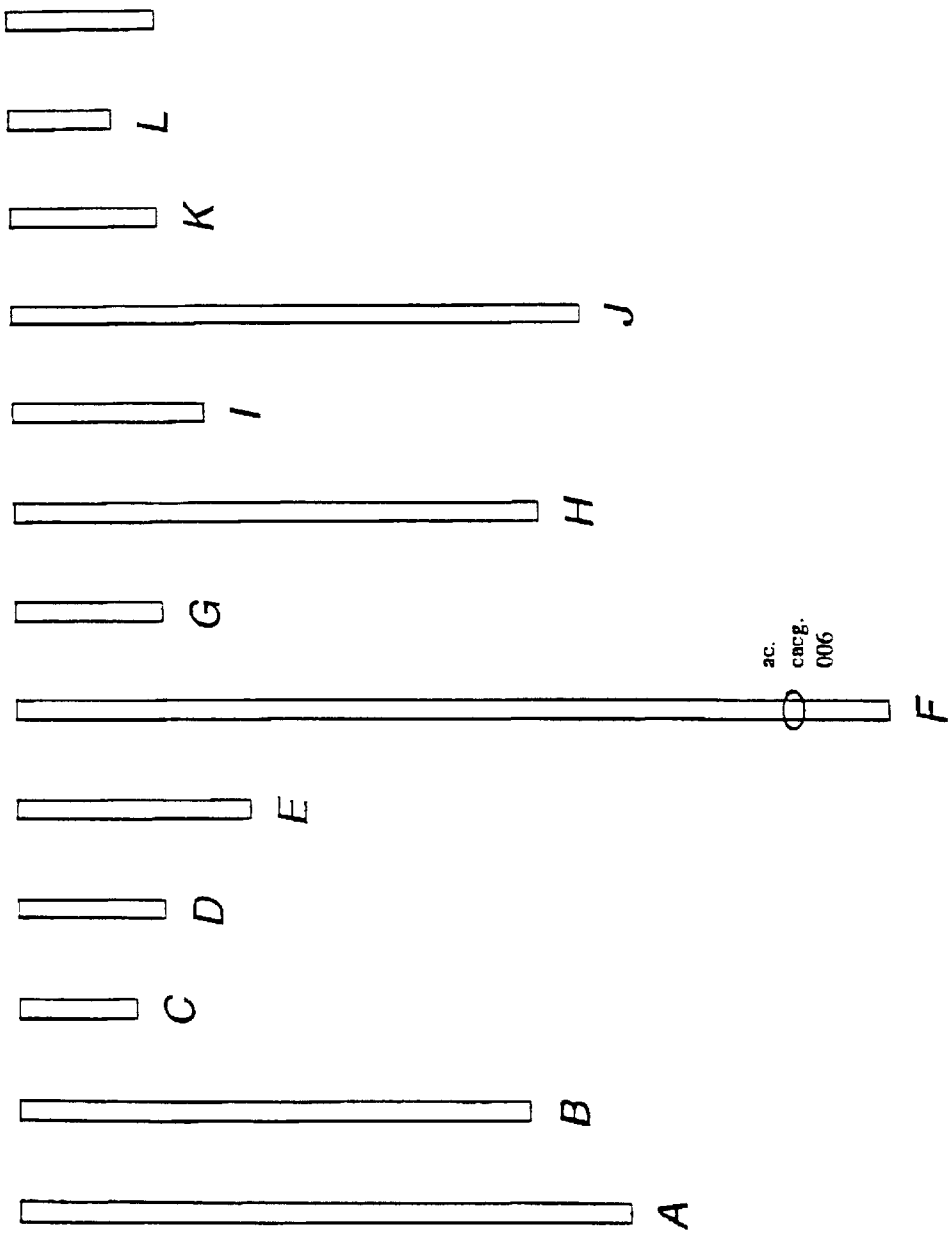
FIG. 2 is a genetic map showing the chromosomal location of the ac.cacg.006 DNA marker in 7-2 trees. The linkage groups in the parental lines are designated A-L.

The chromosomal locations of all three markers are illustrated in FIGS. 1 and 2. Two separate genetic maps were constructed, one for 7-2 (FIG. 2) and one for 7-56 (FIG. 1). The expected number of linkage groups in each loblolly pine genetic map is 12, which equals the number of chromosomes. The 12 linkage groups in both parental lines are designated A through L. Each linkage group in one map should have a corresponding group in the other map. The letter codes, however, do not correspond to the group names. In other words, group A of the 7-56 map can be one of any of the 12 groups in the 7-2 map (A-L). It is important to note that whether one can find a corresponding marker depends on the specific linkage phase, that is not only whether the marker is in the parent genome, but whether the marker and its associated genes are heterozygous.

The effect of the three markers (aca.gct.009, gta.cac.006, and ac.cacg.006) on volume growth in trees of the Satilla site is shown in Table 2. These results demonstrate that single marker selection using either aca.gct.009 or gta.cac.006 would produce a substantial improvement to 16.8 cubic feet or 16.4 cubic feet, respectively. Accordingly, a marker-assisted selection using both aca.gct.009 and gta.cac.006 simultaneously would have elevated volume growth to 18.8, or a 26% gain from the 14.9 base average.

The three AFLP markers described in FIGS. 1 and 2 were detected by autoradiography after separating $^{32}$P-labeled AFLP products in a manual DNA sequencing gel. In those gels, the designation of marker bands was relative to other bands in the same gel, and therefore may vary in different laboratories. To overcome this issue, a set of equivalent (closely-linked) AFLP markers were identified that are defined by their exact product length measured in base pairs. Such precision was made possible by using an ABI PRISM 377 automated DNA sequencer (Perkin Elmer) and fluorescence-labeled PstI primers.

A set of 200 full-sib 7-2×7-56 trees from a second test site, Combahee, were also examined. In addition, 20 selected full-sib trees from the Satilla site were examined again to confirm the results of their AFLP marker genotypes. Samples were from alcohol-treated needles. In these experiments, the samples were analyzed using bulked DNA samples to screen for AFLP markers in the same chromosomal regions. The bulk segregant analysis method has been described by others (Michelmore, R. W. et al. 1991. *Proc. Natl. Acad. Sci. USA* 88:9828–9832). This method allows for rapid screening for AFLP markers at a known chromosomal region, in this case at aca.gct.009 and gta.cac.006, using only two DNA samples instead of the more than 100 samples used in the previous experiment.

Bulked DNA samples were prepared by mixing equal amounts of DNA from at least 11 trees that have the same marker type, for example, aca.gct.009. In the case of aca.gct.009, four bulked samples were produced that were designated BK1-1A, BK1-1B, BK1-3A, and BK1-3B. The samples designated BK1-1A and BK1-1B were derived from trees with a 7-2 phenotype while those designated BK1-3A and BK1-3B have a 7-56 phenotype.

Using bulked screening AFLP analysis, three new markers linked to aca.gct.009 were identified. These new markers were designated ucc101, ucc102, and ucc103.

TABLE 3

Three aca.gct.009-Linked Markers That Were Identified
by Bulked Segregant Screening

| MARKER | SYNONYM | PstI PRIMER (5'-3') | MseI PRIMER (5'-3') | BAND SIZE (bp) |
|---|---|---|---|---|
| ucc101 | gaa.cac.139 | gactgcgtacatgca g-GAA SEQ ID NO: 12 | gatgagtcctgagta a-CAC SEQ ID NO: 15 | 139 |
| ucc102 | ata.gta.134 | gactgcgtacatgca g-ATA SEQ ID NO: 13 | gatgagtcctgagta a-GTA SEQ ID NO: 16 | 134 |
| ucc103 | gaa.gtg.90 | gactgcgtacatgca g-GAA SEQ ID NO: 14 | gatgagtcctgagta a-GTG SEQ ID NO: 17 | 90 |

Figure 3:
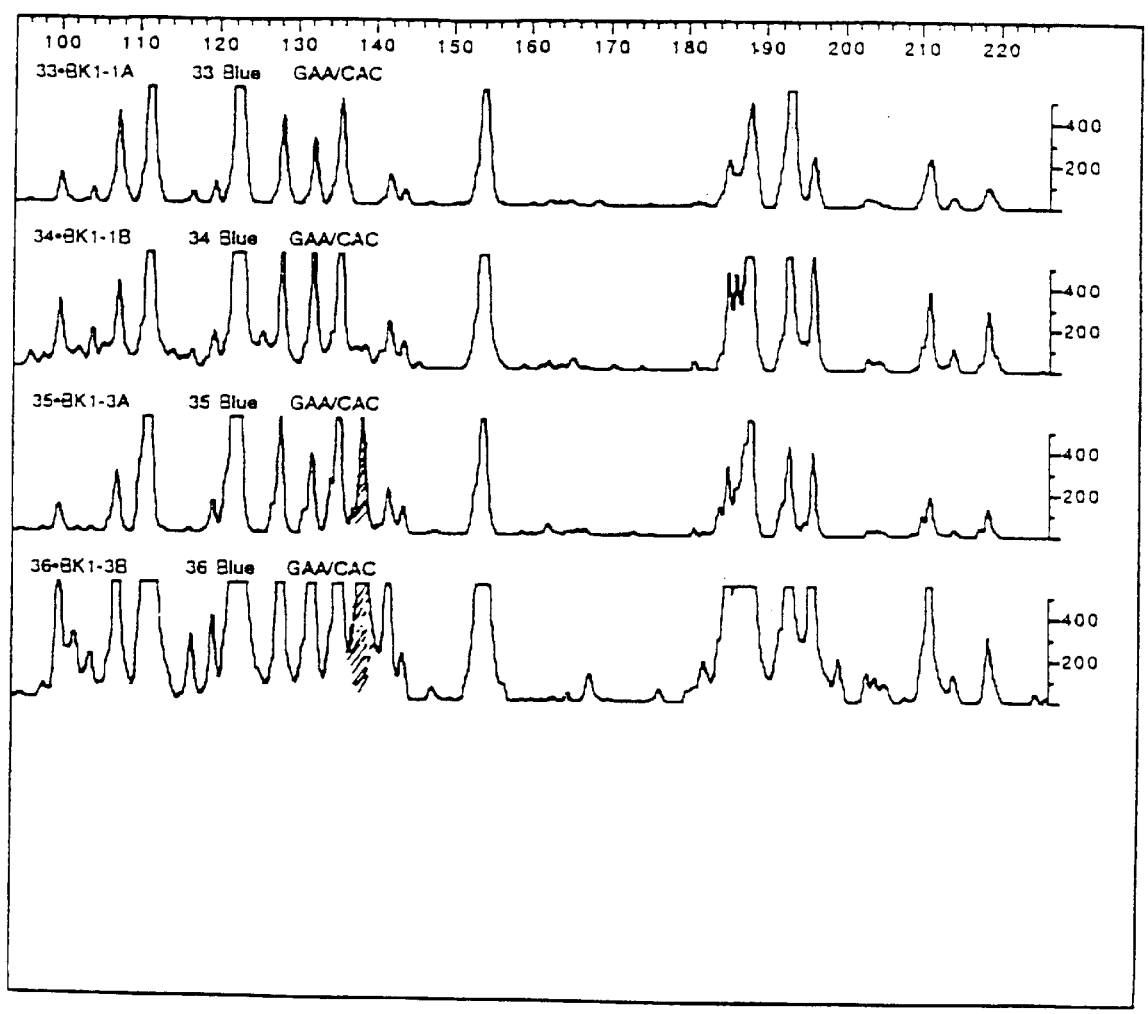
FIG. 3 is the portion of AFLP markers generated by using PstI-GAA/MseI-CAC and ABI PRISM 377 automated DNA sequencer (Perkin Elmer). The linkage of marker ucc101 (gaa.cac.139) to aca.gct.009 is indicated by its absence in two bulked samples (BK1-1A and BK1-1B) that does not carry aca.gct.009 and presence in BK1-3A and BK1-3B.

Selective nucleotides of the PstI and MseI primers are depicted by upper case letters while the adaptor and restriction sequences are depicted by lower case letter. In 30 trees without a aca.gct.009 marker band, marker ucc101 was absent in all 30. However, ucc101 was present in the 30 trees with the aca.gct.009 marker band (FIG. 3). The linkage between ucc101 and aca.gct.009 was confirmed using all 109 available DNA samples from Satilla 7-2×7-56 full-sibs. The genetic distance between the two markers was estimated to be 12 map units, an 88% correlation. The effect of ucc101 on volume growth of trees at the Satilla site was significant (p=0.004). The trees with the ucc101 band were on average 24% higher than those without the band. Because this marker is linked to aca.gct.009, the effect of ucc101 on volume growth is likely due to the expression of the same growth-regulating gene tagged by aca.gct.009.

The effect of ucc101 on volume growth was also detected in 7-2×7-56 trees at the Combahee forest site. All of the available DNA samples of these trees were analyzed for the presence of the ucc101 marker. The ucc101 effect was again highly significant (p=0.009) in trees grown at Combahee. The volume growth of trees having the ucc101 band was 14% higher than for trees without this marker band. These data confirm the linkage of ucc101 with a growth-regulating gene (Table 4).

Similar significant effects on volume growth were linked with two additional markers linked to aca.gct.009, ucc102 and ucc103 (Table 4). These two new markers were identified using bulked DNA samples and a total of 160 different primer pairs to generate more than 4800 AFLP markers. These new markers were analyzed in two sets of 7-2×7-56 full-sib trees from Combahee and Satilla forests.

TABLE 4

The Effect of Three aca.gct.009 Marker Equivalents on the Volume Growth of 7-2 × 7-56 Trees at Two Forest Sites

| Marker | Satilla Forest (n = 109) | | Combahee Forest (n = 124) | |
| --- | --- | --- | --- | --- |
| | Volume Growth (cu. ft) | Increase[1] in Volume Growth | Volume Growth (cu. ft) | Increase in Volume Growth |
| average[2] | 16.02 | — | 12.30 | — |
| ucc101 | 17.77 | 10.9% | 13.55 | 10.2% |
| ucc102 | 17.77 | 10.9% | 13.31 | 8.2% |
| ucc103 | 17.73 | 10.7% | 13.09 | 6.4% |

[1]The percent increase in volume growth as compared to the overall average.
[2]Overall average of the 109 or 124 trees, including those with the marker band.

All three aca.gct.009-linked markers were then cloned and sequenced. AFLP markers were generated by selective amplification using polymerase chain reaction (PCR) of a small subset of the genomic DNA sequence. Each marker was defined by the selective nucleotides in the pair of primers used and the size of the amplified product. For example, marker ucc101 was generated by PstI-GAA and MseI-CAC primers and was 139 base pairs in length, including the primer regions. Therefore, the ucc101 marker is also referred to as gaa.cac.139. These markers are particularly informative when the band is present in one parent, but not in another. For example, the ucc101 band is present in 7-56, but not in 7-2. Therefore, this marker would be especially useful in the study of genetic contributions of 7-56 in, for example, the 7-2×7-56 full sibs.

In order to clone the three aca.gct.009-linked markers, unlabeled PstI primers were made to generate clonable AFLP bands. AFLP products were separated on agarose gel and a section was sliced from the gel for DNA extraction. The presence of target bands ucc101, ucc102, and ucc103 was confirmed using AFLP analysis. The isolated fragments were further amplified using PCR and another round of AFLP with unlabeled primers. The purified AFLP marker-containing DNA samples were inserted into a plasmid vector, pNoTa(T7). More than 200 DNA clones per marker were produced. Among the more than 600 clones, many were found to contain AFLP marker bands that were unrelated to ucc101, 102, or 103. As a result, the clones were screened by size. Table 5 lists the clones that were identified for ucc101, 102 and 103. The DNA sequences for ucc101 (SEQ ID NO: 1), ucc102 (SEQ ID NO: 2), and ucc103 (SEQ ID NO: 3) are shown in FIG. 4.

TABLE 5

Six DNA Clones Identified for Three ACA.GCT.009-Linked AFLP Markers

| Clone | AFLP Marker | Insert Size (bp) |
| --- | --- | --- |
| p101-5-2 | ucc101 | 139 |
| p101-10-1 | ucc101 | 139 |
| p102-1-5 | ucc102 | 134 |
| p103-5-2 | ucc103 | 90 |
| p103-5-6 | ucc103 | 90 |
| p103-5-7 | ucc103 | 90 |

Using information on the DNA sequences for the markers, MseI primers having six selective nucleotides in the variable region were designed to decrease the number of products per PCR reaction and to increase specificity. Sets of AFLP primers depicted in Table 6 were constructed for all three aca.gct.009-linked markers. When compared to the original MseI primers, the number of background bands was dramatically reduced using the AFLP primers of the present invention. Further, the strength of the AFLP bands was increased. These improvements in the AFLP primers significantly reduce the risk of mistyping tree lines.

TABLE 6

Locus-Specific MseI Primers For The Three aca.gct.009-Linked AFLP Markers

| MARKER | MseI primer (5'-3') | |
| --- | --- | --- |
| | Generic | Locus-specific |
| ucc101 | gatgagtcctgagtaa-CAC SEQ ID NO: 15 | gagtcctgagtaa-CACACT SEQ ID NO: 18 |
| ucc102 | gatgagtcctgagtaa-GTA SEQ ID NO: 16 | gagtcctgagtaa-GTATAA SEQ ID NO: 19 |
| ucc103 | gatgagtcctgagtaa-GTG SEQ ID NO: 17 | gagtcctgagtaa-GTGGAC SEQ ID NO: 20 |

Selective nucleotides of the PstI and MseI primers are depicted by upper case letters while the adaptor and restriction sequences are depicted by lower case letter.

In another experiment, another set of 7-2×7-56 full-sib trees from the Satilla site was selected. Needles were collected from 116 trees. Of these trees, 88 were new samples that had not before been analyzed for the presence of aca.gct.009 marker, 17 were replicates that had been analyzed previously, and ten were blind controls. Results of the AFLP analysis using primers of the present invention exemplified in Table 6 showed that the aca.gct.009 marker types of the 17 replicates and the 10 blind samples were in agreement with earlier analysis.

The aca.gct.009 effect on volume growth in the full-sib trees was confirmed by the results of the validation experiment, using 88 full-sib trees from the Satilla forest that had not been previously tested. Combining the two Satilla tree populations, a total of 200 trees were analyzed, which demonstrated that aca.gct.009 causes a significant effect on volume growth.

These data demonstrate the link between the identified DNA markers in loblolly pine and volume growth. The markers identified were mapped to a specific region of the loblolly pine genome. These markers include aca.gct.009, as well as the aca.gct.009-linked markers, ucc101, ucc102, and ucc103. Further, the aca.gct.009-linked markers were identified using AFLP MseI primers (SEQ ID NO: 18, 19 and 20) that were targeted to the ucc101, 102, and 103 DNA sequences (see Table 6). In a preferred embodiment, the presence of aca.gct.009 and its related markers, ucc101, 102, and 103, can be used to select trees for greater potential volume growth. The presence of DNA markers gta.cac.006 and ac.cacg.006 are also indicative of greater volume growth. Accordingly, this invention is applicable to any breeding program where trees carry the same parental line, 7-56. Further, one of skill would be able to use the experiments described herein with aca.gct.009 in loblolly pine to identify other DNA markers for volume growth in other forest species. The methods for screening for DNA markers can include AFLP as well as other genetic mapping methods such as, but not limited to, restriction fragment polymorphism (RFLP), random amplified DNA polymorphism (RAPD), micro satellite methods, and PCR.

The following non-limiting examples are presented to better illustrate the invention:

EXAMPLES

Example 1

Isolation of DNA from Loblolly Pine Tissue Samples

Freshly harvested pine needles were fixed in reagent grade ethanol (1:10 dilution of needle:alcohol). Needles were left for at least 24 hours for adequate fixation. The alcohol was decanted and the needles allowed to air dry overnight at room temperature. After drying, 1 gram of needles was added to a pre-chilled mortar. The needles were frozen in 10 ml liquid nitrogen. Using a pestle, the tissue was ground until thawing. Additional liquid nitrogen was added to keep the sample frozen. This step was repeated at lease three times.

Once ground to a fine powder, the powder and liquid nitrogen were poured into a 40 ml polypropylene tube. The tube was left undisturbed until all of the liquid nitrogen had evaporated. DNA extraction buffer (10 ml) was then added.

Samples were incubated at 65° C. with gentle rocking for 60 to 90 minutes. Samples were cooled for 5 minutes and then extracted with 10 ml of chloroform:octanol (24:1) by rocking for 5 minutes. All tubes were then spun for 10 minutes at 6,000×g. The aqueous phase was then transferred into a clean 40 ml tube using a wide bore Pasteur pipette. One third of the volume of 10 M ammonium acetate was added followed by an equal volume of cold (−20° C.) 2-propanol. The tubes were then mixed by gentle swirling to precipitate the DNA. The DNA precipitate was then transferred to a 15 ml polycarbonate tube containing 5 ml 70% reagent grade ethanol. The tubes were allowed to stand for 5 minutes and then transferred to a clean microfuge tube containing 1 ml TE (10 mM Tris-HCl, pH 8.0 and 1 mM EDTA). The DNA was dissolved at least overnight before further analysis. DNA may also be stored at 4° C. for immediate use or at -20° C. for long-term storage.

Example 2

Bulked DNA Preparation

Bulked DNA samples were prepared by mixing equal amounts of DNA from at least 11 trees that have the same marker type. For example, sample "BK1-3A" would be a bulked sample for aca.gct.009 and was made by mixing 15 7-2×7-56 trees from the Satilla forest, all of which have the type "3".

Example 3

AFLP Analysis

The AFLP procedure has been described in detail by the manufacturer (Perkin Elmer) in a protocol booklet published in October 1995 (AFLP Plant Mapping Kit). The following description is provided based on the details given in the manufacturer's protocol booklet.

An adapter mix is prepared for each sample that includes 1 $\mu$l of 10×T4 ligase buffer (50 mM Tris-HCl pH 7.8, 10 mM $MgCl_2$, 10 mM dithiothreitol, 1 mM ATP, 25 $\mu$g/ml bovine serum albumin), 1 $\mu$l of 0.5 M NaCl, 0.5 $\mu$l of 0.5 bovine serum albumin, 1 $\mu$l of MseI adapter pair, 1 $\mu$l of PstI adapter pair, for a total volume of 4.5 $\mu$l/sample. This adapter mix is then thoroughly mixed by vortex and stored on ice. Next, an enzyme mix is prepared for each sample that includes 0.1 $\mu$l of 10×T4 ligase buffer, 0.1 $\mu$l of 0.5 M NaCl, 0.05 $\mu$l of 0.5 bovine serum albumin, 0.25 $\mu$l of MseI (4 U/$\mu$l), 0.25 $\mu$l PstI (10 U/$\mu$l), 0.165 $\mu$l of T4 DNA ligase (6 U/$\mu$l), 0.025 Rnase A, 0.06 $\mu$l of distilled water, for a total volume of 1 $\mu$l/sample to be assayed. The enzyme mix is gently mixed and stored on ice.

In a set of 200 $\mu$l PCR tubes is added 4.5 $\mu$l of adapter mix, 5.5 $\mu$l of loblolly pine genomic DNA (36–100 ng/$\mu$l), and 1 $\mu$l of enzyme mix (total volume of 11 $\mu$l ). The tubes are mixed thoroughly. The tubes are then incubated at 37° C. for 120 minutes. After incubation, the digestion/ligation product is diluted by adding 89 $\mu$l of $TE_{0.1}$ buffer to each tube. The tubes are vortexed and then stored at −20° C.

Next, the pre-mix is prepared. It includes (for each sample to be assayed) 1 $\mu$l of pre-amp primer pair, 15 $\mu$l of AFLP core mix, for a total volume of 16 $\mu$l. To a set of 200 $\mu$l PCR tubes are added 16 $\mu$l of pre-mix using EDP2-100 and 4 $\mu$l of diluted digestion/ligation product for a total volume of 20 $\mu$l. The reaction tubes are then placed in the GenAmp PCR System 9600. Pre-amp products are diluted by adding 180 $\mu$l of $TE_{0.1}$ buffer to each PCR tube, mixing, and then storing at −20° C.

Amplification is the next step. First, a pre-mix is prepared by mixing 0.5 $\mu$l MseI primer, 0.5 $\mu$l PstI primer, and 7.5 $\mu$l AFLP core mix for a total volume of 8.5 $\mu$l/sample. In a set of PCR tubes are added 8.5 $\mu$l of pre-mix, 1.5 $\mu$l of pre-amp products for a total volume of 10 $\mu$l. These reaction tubes are then placed in the GenAmp PCR System 9600.

What is claimed is:

1. A primer comprising a nucleic acid sequence selected from the group consisting of SEQ ID NO: 18, 19 and 20.

2. A DNA marker consisting of a nucleic acid sequence selected from the group consisting of SEQ ID NO: 1, 2, and 3.

3. A method for identifying loblolly pines with greater volume growth comprising obtaining a tissue sample from loblolly pine and detecting the presence of a DNA marker consisting of SEQ ID NO: 1, 2, or 3, wherein the presence of one of these DNA markers is indicative of a loblolly pine with greater volume growth as compared to a loblolly pine without one of these DNA markers.

4. A method for fingerprinting DNA by AFLP comprising:
   (a) cutting DNA with frequent cutter restriction enzymes to generate DNA fragments;
   (b) amplifying a subset of said DNA fragments by PCR using AFLP primers comprising a variable region of more than three selective nucleotides and a constant region of nucleotides which are fully complementary with base pairs of one end of a DNA strand of a restriction fragment cut by the frequent cutter enzymes, wherein the length of the constant regions of each of the AFLP primers is shorter by one nucleotide for each selective nucleotide over 3 included in the variable region as compared to an AFLP primer with only 3 selective nucleotides so that the length of each AFLP primer remains equal to an AFLP primer with only 3 selective nucleotides and so that selectivity of the AFLP primers comprising a variable region of more than three selective nucleotides is maintained; and
   (c) displaying the amplified subset of DNA fragments as bands by electrophoresis in a polyacrylamide gel.

5. The method of claim 4 wherein the AFLP primers comprise nucleic acid sequences selected from the group consisting of SEQ ID NO:18, 19 and 20.

* * * * *

SEQUENCE LISTING

<160> NUMBER OF SEQ ID NOS: 20

<210> SEQ ID NO 1
<211> LENGTH: 139
<212> TYPE: DNA
<213> ORGANISM: Pinus taeda
<220> FEATURE:

-continued

```
<221> NAME/KEY: unsure
<222> LOCATION: (81)

<400> SEQUENCE: 1
gactgcgtac atgcaggaag caatgtgaat tgtaatagaa gcaattgccc aagaacaatc      60
aataaaatac cacaataaag naagcagtgt ttcccatttg ggtttcctag gtaaacaagt     120
gtgttactca ggactcatc                                                  139

<210> SEQ ID NO 2
<211> LENGTH: 134
<212> TYPE: DNA
<213> ORGANISM: Pinus taeda

<400> SEQUENCE: 2
gactgcgtac atgcagataa tcagtgagat atttagtttt tgatcctgtt catggaaatt      60
gtacacctac aatatccgaa gcacataaag gtggcttatg acttctctcc atttatactt     120
actcaggact catc                                                       134

<210> SEQ ID NO 3
<211> LENGTH: 90
<212> TYPE: DNA
<213> ORGANISM: Pinus taeda

<400> SEQUENCE: 3
gactgcgtac atgcaggaag taatacagtc aaattgggaa ccgcggaggg aaaattgttt      60
tttcaattgt ccacttactc aggactcatc                                       90

<210> SEQ ID NO 4
<211> LENGTH: 24
<212> TYPE: DNA
<213> ORGANISM: Pinus taeda
<220> FEATURE:
<221> NAME/KEY: unsure
<222> LOCATION: (21)..(24)

<400> SEQUENCE: 4
gacgatgagt cctgagtaan nnnn                                             24

<210> SEQ ID NO 5
<211> LENGTH: 20
<212> TYPE: DNA
<213> ORGANISM: Pinus taeda
<220> FEATURE:
<221> NAME/KEY: unsure
<222> LOCATION: (16)..(20)

<400> SEQUENCE: 5
tactcaggac tcattnnnnn                                                  20

<210> SEQ ID NO 6
<211> LENGTH: 17
<212> TYPE: DNA
<213> ORGANISM: Pinus taeda

<400> SEQUENCE: 6
gatgagtcct gagtaac                                                     17

<210> SEQ ID NO 7
<211> LENGTH: 18
<212> TYPE: DNA
<213> ORGANISM: Pinus taeda
```

```
<400> SEQUENCE: 7
gatgagtcct gagtaact                                          18

<210> SEQ ID NO 8
<211> LENGTH: 19
<212> TYPE: DNA
<213> ORGANISM: Pinus taeda

<400> SEQUENCE: 8
gatgagtcct gagtaacta                                         19

<210> SEQ ID NO 9
<211> LENGTH: 20
<212> TYPE: DNA
<213> ORGANISM: Pinus taeda

<400> SEQUENCE: 9
gatgagtcct gagtaactac                                        20

<210> SEQ ID NO 10
<211> LENGTH: 17
<212> TYPE: DNA
<213> ORGANISM: Pinus taeda

<400> SEQUENCE: 10
gagtcctgag taactac                                           17

<210> SEQ ID NO 11
<211> LENGTH: 18
<212> TYPE: DNA
<213> ORGANISM: Pinus taeda

<400> SEQUENCE: 11
gagtcctgag taactact                                          18

<210> SEQ ID NO 12
<211> LENGTH: 19
<212> TYPE: DNA
<213> ORGANISM: Pinus taeda

<400> SEQUENCE: 12
gactgcgtac atgcaggaa                                         19

<210> SEQ ID NO 13
<211> LENGTH: 19
<212> TYPE: DNA
<213> ORGANISM: Pinus taeda

<400> SEQUENCE: 13
gactgcgtac atgcagata                                         19

<210> SEQ ID NO 14
<211> LENGTH: 19
<212> TYPE: DNA
<213> ORGANISM: Pinus taeda

<400> SEQUENCE: 14
gactgcgtac atgcaggaa                                         19

<210> SEQ ID NO 15
<211> LENGTH: 19
<212> TYPE: DNA
<213> ORGANISM: Pinus taeda
```

-continued

<400> SEQUENCE: 15
gatgagtcct gagtaacac                    19

<210> SEQ ID NO 16
<211> LENGTH: 19
<212> TYPE: DNA
<213> ORGANISM: Pinus taeda

<400> SEQUENCE: 16
gatgagtcct gagtaagta                    19

<210> SEQ ID NO 17
<211> LENGTH: 19
<212> TYPE: DNA
<213> ORGANISM: Pinus taeda

<400> SEQUENCE: 17
gatgagtcct gagtaagtg                    19

<210> SEQ ID NO 18
<211> LENGTH: 19
<212> TYPE: DNA
<213> ORGANISM: Pinus taeda

<400> SEQUENCE: 18
gagtcctgag taacacact                    19

<210> SEQ ID NO 19
<211> LENGTH: 19
<212> TYPE: DNA
<213> ORGANISM: Pinus taeda

<400> SEQUENCE: 19
gagtcctgag taagtataa                    19

<210> SEQ ID NO 20
<211> LENGTH: 19
<212> TYPE: DNA
<213> ORGANISM: Pinus taeda

<400> SEQUENCE: 20
gagtcctgag taagtggac                    19